(12) United States Patent
Martin et al.

(10) Patent No.: US 8,467,845 B2
(45) Date of Patent: Jun. 18, 2013

(54) METHOD FOR DATA ACQUISITION AND/OR DATA EVALUATION DURING A FUNCTIONAL BRAIN EXAMINATION WITH THE AID OF A COMBINED MAGNETIC RESONANCE/PET UNIT

(75) Inventors: Diana Martin, Herzogenaurach (DE); Thorsten Feiweier, Poxdorf (DE); Günther Platsch, Röthenbach (DE); Kristin Schmiedehausen, Buckenhof (DE); Sebastian Schmidt, Weisendorf (DE); Michael Szimtenings, Bonn (DE)

(73) Assignee: Siemens Aktiengesellschaft, Munich (DE)

( * ) Notice: Subject to any disclaimer, the term of this patent is extended or adjusted under 35 U.S.C. 154(b) by 1429 days.

(21) Appl. No.: 12/153,487

(22) Filed: May 20, 2008

(65) Prior Publication Data
US 2008/0290281 A1 Nov. 27, 2008

(30) Foreign Application Priority Data
May 22, 2007 (DE) .................. 10 2007 023 657

(51) Int. Cl.
*A61B 5/05* (2006.01)

(52) U.S. Cl.
USPC .......................................... 600/407; 600/410

(58) Field of Classification Search
USPC .................................. 600/407–435
See application file for complete search history.

(56) References Cited

U.S. PATENT DOCUMENTS

| 6,704,592 | B1 * | 3/2004 | Reynolds et al. | 600/411 |
|---|---|---|---|---|
| 6,907,280 | B2 * | 6/2005 | Becerra et al. | 600/407 |
| 7,365,335 | B2 * | 4/2008 | Gagnon et al. | 250/363.04 |
| 7,522,952 | B2 * | 4/2009 | Krieg et al. | 600/411 |
| 7,626,389 | B2 * | 12/2009 | Fiedler et al. | 324/309 |
| 7,626,392 | B2 * | 12/2009 | Nistler et al. | 324/318 |
| 7,667,457 | B2 * | 2/2010 | Linz et al. | 324/307 |
| 7,683,330 | B2 * | 3/2010 | Krieg et al. | 250/363.04 |
| 7,847,552 | B2 * | 12/2010 | Haworth et al. | 324/318 |
| 7,945,079 | B2 * | 5/2011 | Rosen | 382/128 |
| 8,073,525 | B2 * | 12/2011 | Ladebeck et al. | 600/411 |
| 8,090,429 | B2 * | 1/2012 | Vija et al. | 600/427 |
| 2005/0113667 | A1 * | 5/2005 | Schlyer et al. | 600/411 |
| 2005/0273001 | A1 * | 12/2005 | Schmainda et al. | 600/411 |
| 2006/0004275 | A1 * | 1/2006 | Vija et al. | 600/407 |

(Continued)

FOREIGN PATENT DOCUMENTS

| DE | 102005023907 A1 | 12/2006 |
|---|---|---|
| EP | 1002548 A2 | 5/2000 |
| WO | WO 03016946 A2 | 2/2003 |
| WO | WO 2006071922 A2 | 7/2006 |

OTHER PUBLICATIONS

German Office Action, Oct. 26, 2010.

*Primary Examiner* — Sanjay Cattungal
(74) *Attorney, Agent, or Firm* — Harness, Dickey & Pierce, P.L.C.

(57) ABSTRACT

A method is disclosed for data acquisition and/or data evaluation during a functional brain examination with the aid of a combined magnetic resonance/PET unit. In at least one embodiment, functional image data of the brain are acquired in at least two activity states with the aid of both modalities. Further, magnetic resonance image data and PET image data are acquired within time windows determined by the activity states, the acquisition mode and/or the image data being synchronized as a function of a timing of stimulations determining the activity states.

37 Claims, 3 Drawing Sheets

U.S. PATENT DOCUMENTS

| | | | |
|---|---|---|---|
| 2006/0250133 A1* | 11/2006 | Krieg et al. | 324/318 |
| 2006/0251312 A1* | 11/2006 | Krieg et al. | 382/131 |
| 2006/0266947 A1 | 11/2006 | Krieg et al. | |
| 2007/0040123 A1* | 2/2007 | Gagnon et al. | 250/363.04 |
| 2007/0055127 A1* | 3/2007 | Ladebeck et al. | 600/407 |
| 2007/0102641 A1* | 5/2007 | Schmand et al. | 250/363.03 |
| 2007/0299335 A1* | 12/2007 | Declerck et al. | 600/420 |
| 2008/0056550 A1* | 3/2008 | Kadir et al. | 382/131 |
| 2008/0137930 A1* | 6/2008 | Rosen | 382/131 |
| 2008/0164875 A1* | 7/2008 | Haworth et al. | 324/318 |
| 2008/0214927 A1* | 9/2008 | Cherry et al. | 600/411 |
| 2008/0265887 A1* | 10/2008 | Linz et al. | 324/318 |
| 2008/0284428 A1* | 11/2008 | Fiedler et al. | 324/307 |
| 2010/0152577 A1* | 6/2010 | Young et al. | 600/431 |
| 2010/0290683 A1* | 11/2010 | Demeester et al. | 382/131 |

* cited by examiner

FIG 1

METHOD FOR DATA ACQUISITION AND/OR DATA EVALUATION DURING A FUNCTIONAL BRAIN EXAMINATION WITH THE AID OF A COMBINED MAGNETIC RESONANCE/PET UNIT

PRIORITY STATEMENT

The present application hereby claims priority under 35 U.S.C. §119 on German patent application number DE 10 2007 023 657.5 filed May 22, 2007, the entire contents of which is hereby incorporated herein by reference.

FIELD

Embodiments of the invention generally relate to a method for data acquisition and/or data evaluation. For example, they may relate to a method for data acquisition and/or data evaluation during a functional brain examination with the aid of a combined magnetic resonance/PET (Positron Emission Tomography) unit, functional image data of the brain being acquired in at least two activity states with the aid of both modalities.

BACKGROUND

In order to observe the processes in the brain, it is known to carry out an examination with the aid of functional magnetic resonance and PET recordings. During such examinations, image data are acquired usually in the change from the normal state and during various forms of brain activation, that is to say in various activity states, and the results are compared. It is, in particular, also possible here to carry out in addition to the functional magnetic resonance recordings diagnostic magnetic resonance recordings by which a spatial assignment of the activity centers is then enabled. If various activity states distinguish, for example, a state without external stimulation, frequently termed "baseline" or resting state, as well as a state influenced by an optical, acoustic or haptic stimulation or a movement undertaken by a patient, frequently termed activation, a recording operation will be performed during several of these activity states.

In order to avoid settling times and, in particular, to have enough PET tracer available in the PET case, there are determined within these activity states time windows in which, under normal circumstances, optimum results are attained that are then scarcely influenced by settling processes or transition phases. The time intervals between the time windows suitable for the acquisition themselves form time windows and are frequently termed "rejects", since these images are not fed to the evaluation. The sequence of time windows is denoted in technical language as a "paradigm".

Such functional brain examinations are currently carried out sequentially, that is to say each modality on its own. The resulting images and functional data are subsequently fused in a findings and postprocessing application. Both the increased time requirement owing to the separate examinations and the associated difficulties for the patient, and the time spacing between the application of the individual modalities are disadvantageous here. Since magnetic resonance and PET images cannot be recorded simultaneously, the conditions can differ, and the functional brain processes cannot be simultaneously correlated. Furthermore, it is necessary to take heed of the spatial inaccuracy in the subsequent image fusion and/or image correlation.

So-called hybrid modalities have recently been increasingly proposed, consideration also having been given, in particular, to the connection of magnetic resonance and PET installations. Such units particularly enable a simultaneous and isocentric measurement of magnetic resonance and PET data.

SUMMARY

In at least one embodiment of the invention, a method is disclosed that is tuned to the special requirements of combined magnetic resonance/PET examinations of the human brain and with which it is possible to raise the quality of the data and examination, and to simplify and accelerate the operation.

According to at least one embodiment of the invention, magnetic resonance image data and PET image data are acquired within time windows determined by the activity states, the acquisition mode and/or the image data being synchronized as a function of a timing of stimulations determining the activity states.

It is initially provided that there is ultimately a simultaneous acquisition of magnetic resonance image data and PET image data. Within the meaning of embodiments of the present invention, simultaneous means that both image data have been acquired within at least the same time window. Of course, it is also possible to perform truly simultaneous data acquisition. However, what is relevant is the possible assignment to a common time window of the timing, that is to say, for example, for the resting state, to an activation or even to a rejection, a number of types of activation also being conceivable.

This time windowing is determined by the time sequence of the stimulations determining the activity states, that is to say the paradigm already mentioned above. This higher order timing, which ultimately specifies when stimulations are present and in which time windows ideal data are acquired, enables, according to the invention, a synchronization of the two modalities or their image data since, after all, the two modalities place different requirements on the time profile.

Thus, for example, magnetic resonance recordings can be performed very quickly, for example on a time scale of seconds, while the time frame for PET recordings is, however, to be placed in the range of minutes. With the aid of at least one embodiment of the inventive method these different time scales and other requirements can be matched and advantageously combined into a parallel examination by appropriately driving the acquisition mode and/or the data evaluation as a function of the timing.

Consequently, there is no problem in assigning image data to a time window, or therefore in correlating data of the same stimulation and/or the same resting state or also, in particular, in treating them together, something which leads to a great improvement in the data overall, and thus also to a great improvement in the examination quality. A further improvement is attained by virtue of the fact that use is made of a unit that also enables an isocentric recording such that the spatial assignment is likewise simplified. Moreover, the examination time can be substantially reduced owing to the simultaneous recording.

Thus, the basic idea of at least one embodiment of the present invention is for two examination modalities placing different requirements to be driven and/or evaluated centrally over the higher order timing in order thereby to raise the data quality and to reduce the complexity of the examination. A timing or paradigm that defines the corresponding time window is therefore used centrally by an internal or external control device.

A number of advantageous refinements are conceivable for synchronizing the image data. Thus, for example, it can be provided that the image data are stored using the timing together with an information item describing the time window and/or the acquisition instant, and/or are assigned to a time window for evaluation using the timing on the basis of the acquisition instant. Two options are conceivable in essence for undertaking the assignment to the time window. In the case of a time window already defined during the acquisition mode, the image data can be stored with an information item described in the time window. All the image data are then assigned to their respective time window, whereupon they can be appropriately sorted. Of course, it is also sensible in this case to store the acquisition instant. These additional information items need not be stored in the image file itself, but can, for example, be stored in a parallel file. If firstly only the information describing the acquisition instant is stored, it is possible nevertheless for a subsequent assignment to the corresponding time window to be performed via the timing correlated with the actual time profile. In particular, it is also possible for data that have been acquired, for example, in a rejection time window simply to be rejected.

There are in principle two different refinements for driving the magnetic resonance/PET unit. Thus, the magnetic resonance/PET unit can be driven to acquire image data by both modalities within time windows determined by their timing. Thus, data is not acquired at all except within time windows that are well suited to data acquisition. For example, these time windows correspond to a resting state or an activation, in which case no data acquisition is then performed during the so-called settling phases or transition phases. It follows that with the aid of the timing the central control is therefore able to drive both modalities so as to produce simultaneously acquired image data that can be correlated.

It is also conceivable in an alternative that image data are acquired continuously, the image data being synchronized at least partially by assignment to time windows as a function of the timing. Accordingly, after conclusion of the data acquisition, the timing is laid as a template over the continuously acquired image data such that all the image data are assigned to their respective time windows. A subsequent selection and assignment is performed in this case.

It is conceivable in principle in at least one embodiment of the inventive method that the timing is generated dynamically during the data acquisition and, in particular, is stored on a storage means. In this case, the examiner has all the options of freely shaping the sequence of stimulations and rest phases, but it is of course necessary to ensure that the appropriate information items are handed over to the central control device so that the latter are available for evaluation and the synchronization of the image data, that is to say the assignment of the image data to time windows. However, it is normal to use a designated timing, that is to say a designated paradigm, for such a functional brain examination. Such a designated timing can be used by the central control device for ideally driving the acquisition mode and/or the evaluation.

Of course, it is necessary in this case not only that a permanently prescribed timing be present for the appropriate unit, but also that the designated timing can be adapted before the beginning of, and/or during the data acquisition. It is possible however, for example, to conceive a selection from a number of possible timings. For example, it is possible to provide on the central control device a central software component that is responsible for managing the timing and also the driving of the unit. Thereupon, the sequence of the activation states, and thus of the time windows can be configured, stored and adapted at will be a user. Timings of any desired complexity are conceivable in this way.

It is also possible, for example, to define loops, that is to say recurring sequences in the timing, in order to configure a correspondingly long acquisition time. In particular, the timing for the current examination can once more be more precisely adapted as a function, for example, of the current patient. For example, the time windows can be displaced rearward for the purpose of acquisition in the case of more slowly reacting patients.

As already mentioned, the various activity states of the brain are the result of stimulations of missing stimulations. For example, a patient is exposed to an optical and/or acoustic stimulation or is to execute an action that is communicated to him as an acoustic message, for example the raising of his hand. In a particularly advantageous refinement of at least one embodiment of the present invention, a stimulation device for generating stimulations, in particular an optical and/or an acoustic output device, can be driven as a function of the timing. In this way, a further important component is adopted in the central control sequence such that it can be ensured at any time that the stimulation is also present in the corresponding time window, the time window can be determined optimally, and that the optimum image data are used for the final evaluation. In addition, this further automation further simplifies the examination for the investigator. Such a stimulation device can be integrated in the combined magnetic resonance/PET unit, or else be connected externally to the unit or to the central control device. Such a stimulation device can be, for example, a projector that projects optical information items or stimulae in a way visible to the patient. In addition, it is possible to provide an acoustic output means for producing acoustic stimulation, or for instructing the patient by way of a headphone for example.

If the stimulation cannot be undertaken automatically, and/or if stimulation to be undertaken manually, it can also be provided that an advisory message for generating a stimulation is output as a function of the timing. Consequently, the investigator is informed to the effect that a stimulation is required at this instant, and he can take the appropriate measures. However, such an advisory message is also sensible as information when, for example, the stimulation is undertaken automatically via a stimulation device. If, in a further refinement, the stimulation is to be undertaken manually, it is possible that after the output of an advisory message for generating a stimulation the data acquisition be stopped by a user until the input of an acknowledgement message. It is ensured in this way that the stimulation also continues to be present.

As already mentioned, the central control device can be integrated in the magnetic resonance/PET unit such that, for example, the management of timings inside the magnetic resonance/PET units also takes place. However, not all magnetic resonance/PET units are designed for such a functionality. Consequently, it can be provided in a further expedient refinement of the present invention that the timing is stored in a trigger module connected to the magnetic resonance/PET unit, or generated by way of the trigger module, information items relating to the timing, and/or control commands determined as a function of the timing, being transmitted via a communication link to the magnetic resonance/PET unit and being used to synchronize the acquisition mode and/or the image data. The actual central control device is provided within or in the form of the trigger module in this case in a fashion external to the magnetic resonance magnetic resonance/PET unit and connected to the latter via an appropriate interface enabling the central driving of the image acquisition modalities. It is possible in this way to exchange the module, but it is also possible to use other modules for other types of examination. Of course, the stimulation device that is even integrated in the trigger module if appropriate can also, if present, be automatically driven by the trigger module.

There is generally a need for a tracer in order to prepare PET pictures effectively. The half-life of the tracer essentially determines how long it is possible to collect PET image data of high quality. Various tracers are possible for various applications and requirements. Some tracers, for example $^{15}O$, have a half-life in the range of minutes. It is then customary for the tracer to be reinjected, for example at each production of each activation state. The inundation of the tracer or its half-life can then be determined with the aid of a time window in which it is possible to acquire evaluatable image data. In other words, the instant of the tracer administration plays a large role in determining the time windows in the timing in the case of short-lived tracers. In some cases, it is also sensible to administer contrast agent even for functional magnetic resonance examinations.

Consequently, it can be provided with particular advantage that a device for contrast agent administration and/or tracer administration is driven for the administration of a contrast agent and/or tracer as a function of the timing. This means that the device for contrast agent administration and/or tracer administration is also incorporated into the central control such that, on the one hand, a greater accuracy in the determination of the time windows, and thus a higher examination quality are achieved, on the other hand the requirements placed on the investigator are reduced. For example, an injection that is to be undertaken and is adapted to the timing can always be performed in a fashion synchronized with various activation phases.

In general, it is also sensible when an advisory message for administering a tracer and/or contrast agent is output as a function of the timing. If the tracer and/or the contrast agent are/is to be administered manually, after the output of an advisory message for administering a tracer and/or contrast agent the data acquisition can be stopped by a user until the input of an acknowledgement message. Consequently, the unit can stop the data acquisition until the injection has been performed. However, it is also conceivable, for example, to let a countdown for the injection run such that a user should administer the injection within this countdown.

It is expediently possible to fix designated instants for administering a contrast agent and/or a tracer in the timing such that these are a fixed component of the timing. This fixing can be undertaken by an experienced examiner, but also be performed automatically with the aid of the planned sequence of the activation states.

In a further advantageous refinement of at least one embodiment of the invention, movement information items of a movement detection system are taken into account for driving the data acquisition and/or the data evaluation. Alternatively, or in addition, it is possible to take account of movement information items inferred from magnetic resonance recordings. Such movement detection systems can comprise, for example, a camera that observes the patient. However, other types of movement detection are conceivable, and are basically known from the prior art. Movements of the patient are consequently detected, analyzed and taken into account either retrospectively in the data analysis or prospectively in the data acquisition, in particular with regard to the acquisition volume. Furthermore, the movement information items can be used in the data evaluation for movement correction. Particularly when examining the motor system, a plausibility check and/or cooperation check can be carried out with reference to the activation state on the basis of the movement information. If the patient is, for example, to lift his hand, this can be ascertained by the movement detection system. If no raising of a hand occurs, the patient can, for example, be requested to raise his hand, but in any case the image data, which then do not correspond to the correct activity state, are rejected.

Additionally or as an alternative to a movement detection system, it is also possible to provide a patient cooperation detection device, in particular an eye tracking system and/or a patient feedback device in particular a response button. It is then also possible for patient information items of a patient cooperation detection device and/or of a patient feedback device to be taken into account when driving the data acquisition and/or the data evaluation. A patient cooperation detection device can, for example, be used to ascertain whether a patient is cooperating, for example, is in fact tracking an optical stimulus with his eyes. Moreover, the patient himself can use a patient feedback device to provide an information item on the extent of which a stimulation has been successful or has reached them at all. In special cases, it is possible even to make use the information of a movement detector system and/or patient cooperation detection device and/or a patient feedback device in order firstly to assign time windows to specific activity states.

Information items can be used in general in order, for example, to extract data from the data evaluation, and thus to improve the overall quality of the examination. However, it is also possible to repeat specific parts of the timing after a failure. In particular, such information items can also serve a purpose of undertaking modifications to stimulation devices or other components. In order also to be able in retrospect to undertake a corresponding evaluation, it is advantageous when movement information items and/or patient information items and/or information items derived therefrom are stored with reference to a time window and/or together with image data. The information items relating to the evaluation then are still available at a later point in time.

The synchronization of the image data such as can be achieved by at least one embodiment of the inventive method means, in particular that the image data of both modalities are synchronously processed in the data evaluation. This means, firstly, that they can be processed jointly and corrected with one another, but also that during erasure of image data of one modality temporally corresponding image data of the other modality are also erased. Thus, for example, it is possible for specific parts of the timing of paradigm to be rejected in a post-processing step or immediately during the measurement when it has been ascertained that a patient has behaved uncooperatively. In such a case, both the PET image data and magnetic resonance image data of the relevant time window are rejected. The data of both modalities are thus always treated synchronously with one another.

The data evaluation can be performed using methods known in principle. Thus it can be provided that image data of identical activation states are statistically averaged in the course of the data evaluation. Likewise it is possible that a time series analysis is carried out in the course of the data evaluation by taking account of the timing, activation cards being compiled in particular. Of particular use in carrying out the data evaluation are the so-called t-test and/or GLM (General Linear Model) analysis. In particular, statistical evaluation of data can already be performed during the data acquisition from previous image data relating to specific activity states such that evaluation data that are already current are always present. The parallel application of a number of timings or paradigms is also conceivable when use is made of more complex evaluation methods such as, for example, GLM methods.

In at least one embodiment of the inventive method, the data acquisition can be ended automatically upon a specific data quality being reached, and/or following the end of a prescribed timing and/or by user interaction. In particular, it is possible during the data acquisition to determine for the data evaluation a value that specifies the current data quality—for example in a statistical regard—such that the data acquisition can be ended automatically upon recognition of a specific data quality. This can happen, for example, if, as already mentioned, a prescribed timing runs in a loop. It is also possible for a user to end the data acquisition given that a sufficient data quality has been reached.

In addition to embodiments of the method, at least one embodiment of the invention also relates to a medical examination device for data acquisition and/or data evaluation during a functional brain examination, comprising a combined magnetic resonance/PET unit a central control device, designed for carrying out at least one embodiment of the inventive method. The medical examination device comprises a central control device that can be arranged internally, for example, in a fashion combined with a control unit of the magnetic resonance/PET unit, or else externally that is to say in a fashion connected to the magnetic resonance/PET unit via an interface.

The central control device is then designed to carry out at least one embodiment of the method according to at least one embodiment of the invention. If the central control device is arranged externally, it can then, for example be part of a trigger module with the aid of which the various activity states of the brain can be triggered. Apart from such a trigger model, at least one embodiment of the inventive examination device can also comprise a device for contrast agent administration and/or for tracer administration and a stimulation device for producing the stimulations.

In order to obtain information items relating to the patient, it would, however, be possible to provide a movement detection system and/or a patient cooperation detection device in particular an eye tracking system and/or a patient feedback device, in particular a response button. All these devices are then connected to the central control device via a communication link and can be driven via them. Consequently, a central architecture is implemented that enables a temporally perfectly tuned examination of high quality to be carried out. This is achieved by the synchronization, provided according to at least one embodiment of the invention, of the acquisition mode and/or the image data.

BRIEF DESCRIPTION OF THE DRAWINGS

Further advantages and details of the present invention emerge from the example embodiments described below, and with the aid of the drawings, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
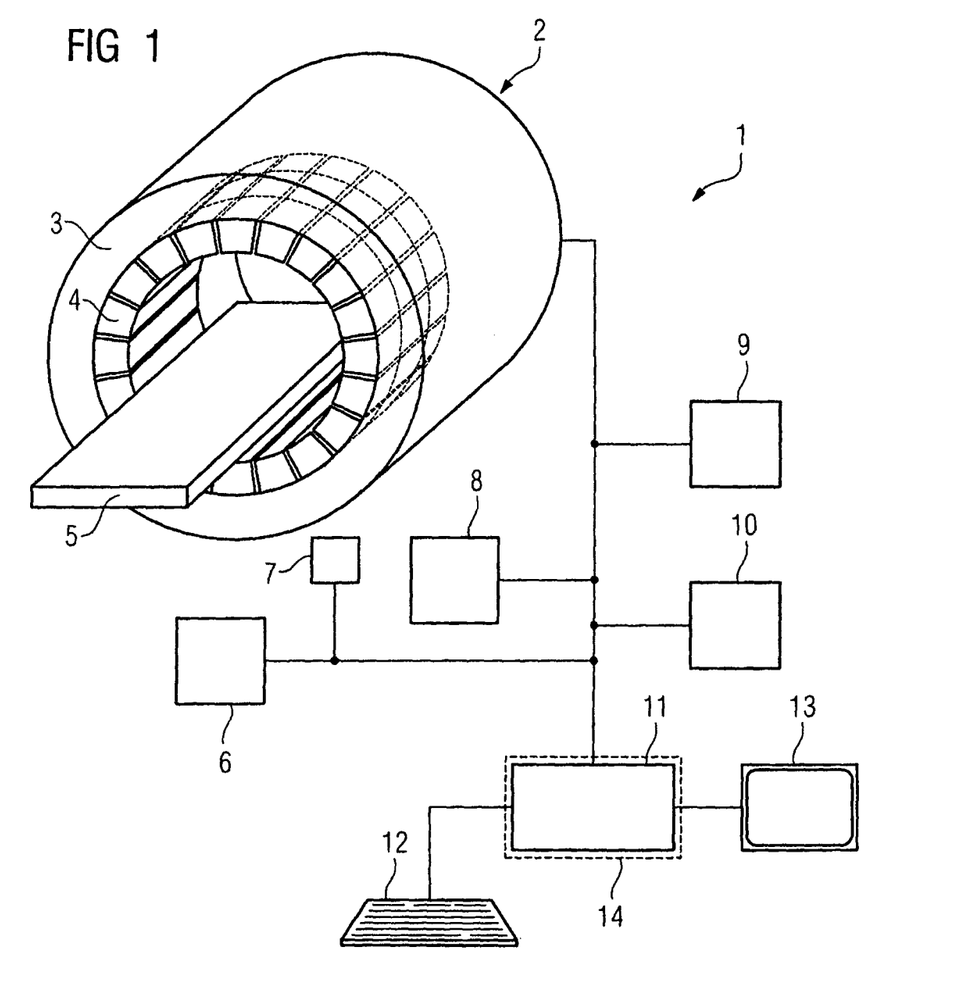
FIG. 1 shows an embodiment of an inventive examination device.

FIG. 1 shows the schematic sketch of an embodiment of an inventive medical examination device 1. It comprises a combined magnetic resonance/PET unit 2 that comprises a solenoid magnet 3 and (not shown in more detail here) gradient coils and radio-frequency coils for acquiring magnetic resonance image data. A PET detector 4 for acquiring PET image data is provide inside the magnet 3. The magnet 3 and the PET detector 4 define a patient opening into which a patient on a patient couch 5 can be moved in order to be able to carry-out a functional brain examination.

In addition, the medical examination device 1 can include further optional components that can be either incorporated in the combined magnetic/PET unit, with which, furthermore, it is possible to acquire magnetic resonance and PET image data simultaneously and isocentrically, or can be provided as external devices. These optional components include a patient cooperation detection device 6, a patient feedback device 7, a movement detection system 8, a stimulation device 9 and a device for administering a PET tracer 10. The patient cooperation detection device can be, for example, an eye tracking system with the aid of which it can be ascertained whether the patient is, for example, also experiencing an optical stimulation. A patient feedback device can be, for example, a response button. The movement detection device 8 can be a camera or the like, but it is also possible that it is configured for processing magnetic resonance overview images that have been recorded in intermediary fashion and can also be evaluated with reference to a patient movement.

The stimulation device 9 can include an optical and/or acoustic output device. Visual stimuli can be generated as stimulations via an optical output device, for example a projector. An acoustic output device can output commands to the patient, but can also stimulate directly via noises, for example via a headphone. The device for tracer administration (a device for administering contrast agent can also be provided if appropriate) 10 is usually an autoinjector that automatically administers the radioactive tracer upon receiving a control command.

These components, if present, can be controlled via a central control device 11. This is connected to the devices 2, 6-10 via communication links, and can drive the devices via control commands and/or received data. Connected to the central control device 11 are, furthermore, an input device 12, for example, a keyboard and a monitor 13.

The control device 11 can be provided in the unit 2, but can also be configured such that it can be connected to the unit 2 externally and thus via an interface. For example, the control device 11 can be part of a trigger module indicated at 14. The control device 11 is designed in such a case to transmit control commands and/or information items relating to a timing to the unit 2.

In particular, the control device 11 is designed such that during the data acquisition and/or data evaluation in a functional brain examination wherein functional image data of the brain in the two activity states are being acquired with the aid of magnetic resonance and PET, and magnetic resonance image data and PET image data are being acquired within time windows determined by the activity states, it synchronizes the acquisition mode and/or the image data as a function of the timing of stimulation determined by the activity states.

Consequently, the aim is to synchronize the acquisition mode and/or the image data by way of central driving. This is orientated in relation to a timing that comprises at least the time windows dependent on the activity states and their duration. Such a timing is, for example, also denoted as a paradigm.

Before the examination begins, a user can employ the input device 12 and the monitor 13 to choose a timing from a set of prescribed timings, or to define a new timing. Of course, it is also possible in this case to change a designated timing—even during the data acquisition. It is also conceivable in principle for the timing only to occur dynamically during the data acquisition. Nevertheless, it is intended below firstly to assume a designated timing.

Figure 2:
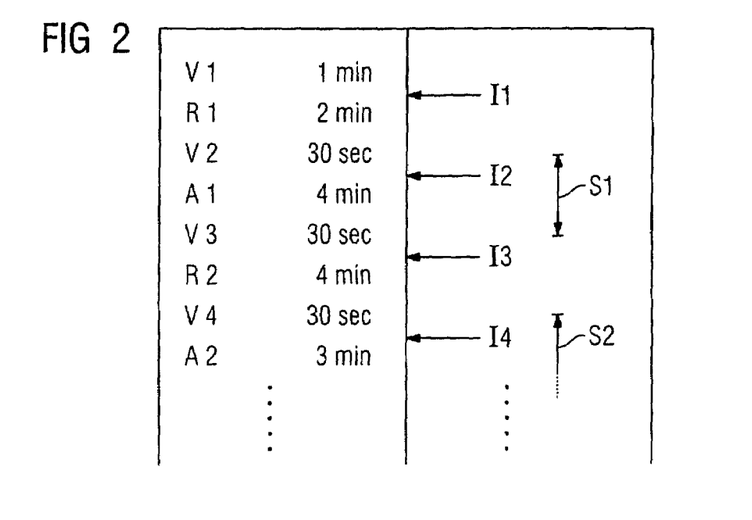
FIG. 2 shows a timing (paradigm) used in an embodiment of the inventive method.

An example of such a timing 15 is illustrated schematically in FIG. 2. By way of example, the aim here is to assume a brain examination in which a distinction is made between two activity states, specifically a resting state R and an activation A. However, in this case the timing 15 also includes a further type of time windows, specifically rejection windows V. Settling processes take place in these time intervals or not enough PET tracer is present or the like, and so no sensible data can be acquired. Consequently, the timing 15 thus includes a number of time windows (V1, R1, V2, . . . ) with their durations. Time windows are ultimately determined by the stimulations S for activation, and the injection instants I for the PET tracer. These, as well, are presently included in the timing 15.

It is also conceivable simply for a user to input the stimulation times S1, S2, . . . and the injection instants I1, I2, . . . , the control device 11 automatically determining the corresponding time windows therefrom. It is frequently sensible to be able to set the time windows themselves, since there is no desire at all to acquire data during some activity states. In the present example embodiment, an injection with PET tracer is respectively placed before the resting state phases R1, R2, . . . and the activation phases A1, A2, . . . , since the tracer has a very short half-life in the range of minutes. In addition, during the activation phases A1, A2, . . . a respective stimulation S1, S2, . . . is present. Clearly, the beginning of the stimulation occurs somewhat earlier than the assigned time window so that settling effects are avoided. The injection of a tracer typically occurs simultaneously with the start of the time window, or somewhat before that, if the arterial inflow is also to be detected.

If a device for tracer administration 10 is provided, the injection instants I1, I2 . . . determine the instants at which the control device 11 drives the automatic injector for administering the tracer. If no automatic tracer administration is provided, or if the user is to be informed in the event of an automatic tracer administration, an advisory message can be generated on the monitor 13. If the tracer is administered manually, the data acquisition—that is to say the sequence of the time windows—is stopped until a user has confirmed the administration of the tracer.

Similarly, the stimulation times S1, S2 ... determined the instants at which the stimulation device 9 is driven to produce the corresponding stimulation. These remain present for all the times S1, S2, .... Here, as well, it is provided, if appropriate, in the case of a manual stimulation that an advisory message is generated, it being impossible to continue until after acknowledgement.

If, however, it is ascertained via the patient cooperation detection device 6, the patient feedback device 7 or the movement detection system 8 that the stimulation is ineffective or that the patient is not cooperating, it is likewise possible for other components to be appropriately driven, for example, warning information can be supplied, the appropriate data can be rejected, the acquisition mode can be stopped until the cooperation of the patient is assured, etc. Of course, it is also possible for this to entail altering the timing 15 during the data acquisition, which is, after all also possible in an embodiment of the inventive method.

Figure 3:
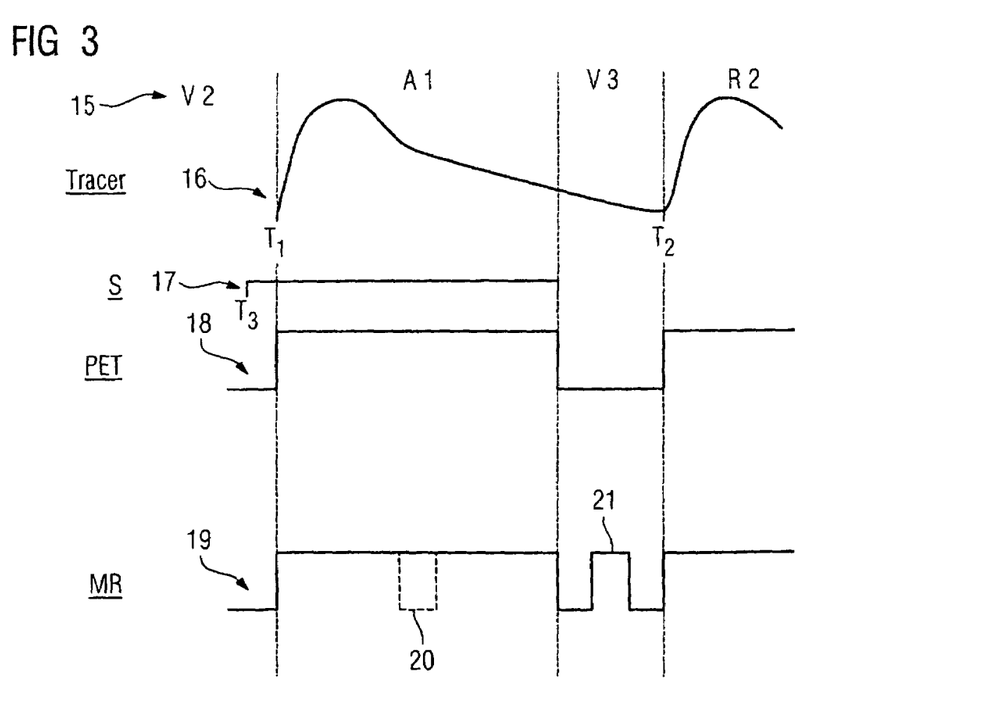
FIG. 3 shows a sketch for explaining the control of the acquisition mode, a stimulation device and a device for tracer administration within the scope of an embodiment of the present invention.

FIG. 3 shows a schematic sketch of an option for controlling the data acquisition with the aid of the timing 15. In this case, only a section of the timing 15 is shown here, specifically the second rejection window V2, the first activation phase A1, the third rejection window V3 and the second resting state phase R2. The graph 16 shows the profile of the tracer concentration in the brain. At the instant T1 in the time window V2, the control device 11 drives the device for tracer administration 10 to administer the tracer that then begins to flow. At the beginning of the time window A1, which corresponds here to the instant T1, there is a steep rise in the tracer concentration that can also be detected. At the end of the time window A1, at the beginning of the time window V3, the tracer concentration has sunk below the required value. At the instant T2, there follows a renewed administration of the tracer, and this corresponds to the beginning of the time window R2.

The graph 17 shows the activity of the stimulation device 9 for stimulating the patient. The stimulation begins at an instant T3, which lies before the beginning of the time window A1, but after the instant T1, for example by the projection of an optical stimulus. At the beginning of the time window A1, the settling phase is concluded and reliable data could be acquired.

Thus, it is clearly possible to acquire data of high quality in the time windows A1 and R2.

The control device 11 is designed such that it drives the unit 2 to acquire PET image data and magnetic resonance image data simultaneously within the time windows A1 and R2. This is shown in the graphs 18 and 19. What is chiefly relevant for the simultaneity in the sense of an embodiment of the present invention is that both PET image data and magnetic resonance image data are acquired within the time window. In this case, it is even possible to conceive interrupting the data acquisition of one modality temporally as shown by way of example in region 20 or to acquire at different times within the same time window. In each case, as a result of driving by the control device 11 there are present from the same time window image data which can be appropriately assigned to one another and be correlated with one another for evaluation.

To this end it is provided in the method that the image data are respectively stored with an item of information describing the time window and also an acquisition instant. Thus, there are present in synchronized fashion, image data that can be uniquely assigned to a window, for example A1, R2 or other time windows.

It may be remarked, however, at this juncture that a modality can also be driven outside the time windows provided for the data acquisition (in this case, A1, A2, . . . and R1, R2 . . . ). This is indicated by way of example, in region 21 for the acquisition of magnetic resonance image data; here, structural images are acquired in order to obtain information relating to the movement of the patient, that is to say movement information.

In addition, it may be remarked again that it is not necessary for a data acquisition to be performed during each activation phase or resting state phase.

Figure 4:
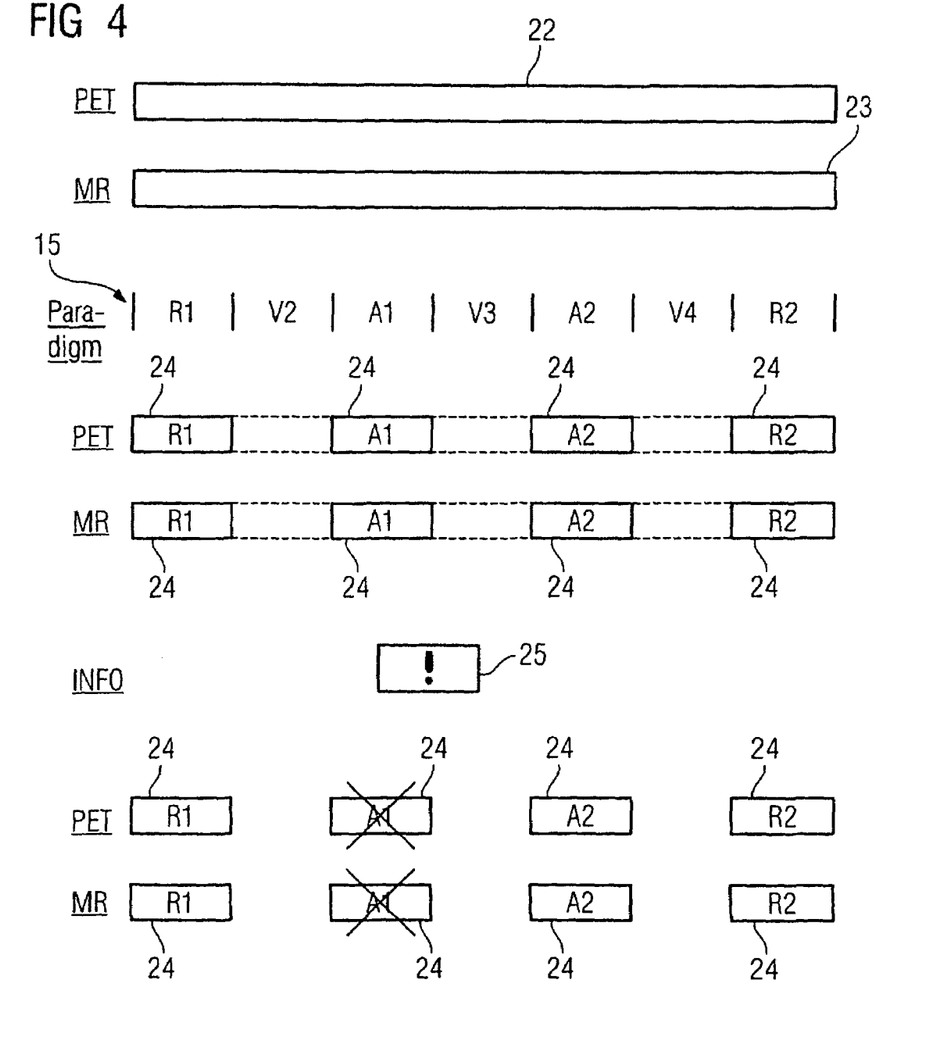
FIG. 4 shows a schematic sketch for explaining an embodiment of the inventive method in the case of continuous image data acquisition.

Another variant in which the image data are acquired continuously is shown by the schematic sketch in FIG. 4. After the data acquisition, that is to say at the beginning of the data evaluation, there are then present continuously acquired PET image data 22 and continuously acquired magnetic resonance image data 23. These are all stored with the instant of their acquisition. It is now possible on the basis of this instant to lay the timing 15 like a mask over the image data 22 and 23, whereupon it is possible to determine the data 24 lying in the relevant time windows R1, R2, . . . and A1, A2, . . . from the image data 22, 23. The data lying in the rejection phases can be rejected. Thus, a synchronization of the image data is achieved here as well.

FIG. 4 also shows an option for the synchronous handling of the synchronized image data 24 during the evaluation. Thus, there is shown at 25 a temporarily determined information item that indicates a lack of readiness on the part of the patient to cooperate. This information can be derived, for example, from movement information of the movement detection system 8, from patient information of the patient cooperation detection device 6 and/or from the patient feedback device 7, or else from information input by the user via the input device 12.

In each case, the information 25 signifies that there is no cooperation on the part of the patient during the time window A1. These data would distort the examination result and lower the overall quality of the data. Consequently, these data are now erased. The PET image data 26 corresponding to the time window A1 and also the magnetic resonance image data 27 corresponding to the time window A1 can be jointly erased in a simple way on the basis of the synchronization of the image data and their synchronous handling.

In addition to this example, suitable for a simple explanation, of the synchronous handling in the event of erasure, yet further advantages result from the synchronization in accordance with an embodiment of the inventive method. Thus, a joint handling of magnetic resonance and PET image data is possible during the evaluation. Again, a direct temporal correlation can be produced during the individual phases, particularly even if an instant has been stored.

Of course, these statements relating to the synchronous handling of the image data can also be applied to the example embodiment according to FIG. 3.

The evaluation of the data can thus be carried out more easily, more quickly and with less outlay, ultimately in a fashion similar to the known methods, the image data of both modalities being processed synchronously. Thus, image data of the same activation states can be averaged statistically during the data evaluation. For example, a time series analysis can be carried out in accordance with the data evaluation by taking account of the timing, activation cards being compiled, in particular. A t-test and/or a GLM analysis can be carried out to this end. In particular, the data evaluation can be performed in parallel with the data acquisition, such that the data quality improves over time from a statistical point of view with an increase in the existing image data. This improvement in data quality can be monitored by a user, or else automatically. The data acquisition can then be ended automatically upon a specific data quality being reached or by user interaction. Alternatively, of course, it can also be provided that data acquisition is ended upon the ending of a prescribed timing.

It is also possible during the data evaluation to make use of movement information of the movement detection system 8 and patient information of the patient cooperation detection device and of the patient feedback device in order, for example, to exclude image data synchronously, or to correct them synchronously with reference to a patient movement. Of course, data of such type can also already be used during the data acquisition, for example, by adapting the next imaging volume upon a movement of the patient, or by directly rejecting data when patient cooperation is not ascertained. It may also be remarked at this juncture that the said information can also serve for the subsequent determination of—in this example—resting state phases and activation phases.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for at least one of data acquisition and data evaluation, comprising:
   acquiring functional image data of the brain, during a functional brain examination, in at least two activity states using different modalities of a combined magnetic resonance/PET unit, magnetic resonance image data and PET image data being acquired as the functional image data of the brain within time windows determined by the at least two activity states, at least one of an acquisition mode and the image data being synchronized as a function of a timing of stimulations determining the at least two activity states.

2. The method as claimed in claim 1, further comprising:
   at least one of
      storing the image data, using the timing, together with an information item describing at least one of a time window and an acquisition instant, and
      assigning the imager data to a time window for evaluation using the timing on the basis of the acquisition instant.

3. The method as claimed in claim 1, wherein the magnetic resonance/PET unit is driven to acquire image data by both modalities within time windows determined by their timing.

4. The method as claimed in claim 1, wherein image data are acquired continuously, the image data being synchronized at least partially by assignment to time windows as a function of the timing.

5. The method as claimed in claim 1, wherein the timing is generated dynamically during the data acquisition.

6. The method as claimed in claim 1, wherein a designated timing is used.

7. The method as claimed in claim 6, wherein the designated timing is adapted at least one of before the beginning of, and during the data acquisition.

8. The method as claimed in claim 6, wherein a selection is made from a number of possible timings.

9. The method as claimed in claim 6, wherein a stimulation device for generating stimulations is driven as a function of the timing.

10. The method as claimed in claim 6, wherein an advisory message for generating a stimulation is output as a function of the timing.

11. The method as claimed in claim 10, wherein after the output of an advisory message for generating a stimulation the data acquisition is stopped by a user until the input of an acknowledgement message.

12. The method as claimed in claim 1, wherein the timing is at least one of stored in a trigger module connected to the magnetic resonance/PET unit, and generated by way of the trigger module, at least one of information items relating to the timing and control commands determined as a function of the timing being transmitted via a communication link to the magnetic resonance/PET unit and being used to synchronize at least one of the acquisition mode and the image data.

13. The method as claimed in claim 1, wherein a device for at least one of contrast agent administration and tracer administration is driven for the administration of at least one of a contrast agent and tracer as a function of the timing.

14. The method as claimed in claim 12, wherein an advisory message for administering at least one of a tracer and contrast agent is output as a function of the timing.

15. The method as claimed in claim 14, wherein after the output of an advisory message for administering at least one of a tracer and contrast agent, the data acquisition is stopped by a user until the input of an acknowledgement message.

16. The method as claimed in claim 13, wherein designated instants for administering at least one of a contrast agent and a tracer is fixed in the timing.

17. The method as claimed in claim 1, wherein movement information items of a movement detection system are taken into account for driving at least one of the data acquisition and the data evaluation.

18. The method as claimed in claim 17, wherein the movement information items are used in the data evaluation for movement correction.

19. The method as claimed in claim 17, wherein when examining the motor system on the basis of the movement information items, at least one of a plausibility check and a cooperation check is carried out with reference to the activation state.

20. The method as claimed in claim 1, wherein patient information items of at least one of a patient cooperation detection device and a patient feedback device is taken into account when driving at least one of the data acquisition and the data evaluation.

21. The method as claimed in claim 17, wherein at least one of movement information items, patient information items and information items derived therefrom are stored at least one of with reference to a time window and together with image data.

22. The method as claimed in claim 1, wherein the image data of both modalities are synchronously processed in the data evaluation.

23. The method as claimed in claim 22, wherein, during erasure of image data of one modality, temporally corresponding image data of the other modality are also erased.

24. The method as claimed in claim 1, wherein image data of identical activation states are statistically averaged in the course of the data evaluation.

25. The method as claimed in claim 1, wherein a time series analysis is carried out in the course of the data evaluation by taking account of the timing, activation cards being compiled in particular.

26. The method as claimed in claim 1, wherein at least one of a t-test and a GLM analysis is carried out for the data evaluation.

27. The method as claimed in claim 1, wherein the data acquisition is ended automatically at least one of upon a specific data quality being reached, following the end of a prescribed timing and by user interaction.

28. A medical examination device, comprising:
a combined magnetic resonance/PET unit; and
a central control device, designed for carrying out the method as claimed in claim 1.

29. The method as claimed in claim 2, wherein the magnetic resonance/PET unit is driven to acquire image data by both modalities within time windows determined by their timing.

30. The method as claimed in claim 2, wherein image data are acquired continuously, the image data being synchronized at least partially by assignment to time windows as a function of the timing.

31. The method as claimed in claim 5, wherein the timing is stored on a storage device.

32. The method as claimed in claim 9, wherein the stimulation device includes at least one of an optical and an acoustic output device.

33. A computer readable medium including program segments for, when executed on a computer device, causing the computer device to implement the method of claim 1.

34. A medical examination device, comprising:
a combined magnetic resonance/PET unit; and
a control device to acquire functional image data of the brain, during a functional brain examination, in at least two activity states using different modalities of the combined magnetic resonance/PET unit, magnetic resonance image data and PET image data being acquired as the functional image data of the brain within time windows determined by the at least two activity states, at least one of an acquisition mode and the image data being synchronized as a function of a timing of stimulations determining the at least two activity states.

35. The device as claimed in claim 34, further comprising:
at least one of
a storage device to store the image data, using the timing, together with an information item describing at least one of a time window and an acquisition instant, and
a device to assign the imager data to a time window for evaluation using the timing on the basis of the acquisition instant.

36. A medical examination device, comprising:
a combined magnetic resonance/PET unit; and
means for acquiring functional image data of the brain, during a functional brain examination, in at least two activity states using different modalities of the combined magnetic resonance/PET unit, magnetic resonance image data and PET image data being acquired as the functional image data of the brain within time windows determined by the at least two activity states, at least one of an acquisition mode and the image data being synchronized as a function of a timing of stimulations determining the at least two activity states.

37. The device as claimed in claim 36, further comprising:
at least one of
means for storing the image data, using the timing, together with an information item describing at least one of a time window and an acquisition instant, and
means for assigning the imager data to a time window for evaluation using the timing on the basis of the acquisition instant.

* * * * *